(12) United States Patent
Devine

(10) Patent No.: US 10,485,695 B2
(45) Date of Patent: *Nov. 26, 2019

(54) PROJECTION FRAME EYELID HEATER

(71) Applicant: John Devine, Tempe, AZ (US)

(72) Inventor: John Devine, Tempe, AZ (US)

(73) Assignee: OCuSOFT, Inc., Rosenburg, TX (US)

( * ) Notice: Subject to any disclaimer, the term of this patent is extended or adjusted under 35 U.S.C. 154(b) by 850 days.

This patent is subject to a terminal disclaimer.

(21) Appl. No.: 15/098,390

(22) Filed: Apr. 14, 2016

(65) Prior Publication Data

US 2016/0220414 A1 Aug. 4, 2016

Related U.S. Application Data

(63) Continuation-in-part of application No. 14/311,573, filed on Jun. 23, 2014, now Pat. No. 10,369,041,
(Continued)

(51) Int. Cl.
*A61F 7/00* (2006.01)
*A61F 7/02* (2006.01)
*A61F 9/04* (2006.01)

(52) U.S. Cl.
CPC ............... *A61F 7/007* (2013.01); *A61F 7/02* (2013.01); *A61F 9/04* (2013.01);
(Continued)

(58) Field of Classification Search
CPC .... A61F 7/007; A61F 9/04; A61F 7/02; A61F 2007/0223; A61F 2007/0077;
(Continued)

(56) References Cited

U.S. PATENT DOCUMENTS 2,038,275 A * 4/1936 Fogg ..................... H05B 3/342
165/46
3,173,419 A 3/1965 Dubilier et al.
(Continued)

FOREIGN PATENT DOCUMENTS

DE 29914199 8/1999
JP WO98/10723 3/1998
(Continued)

OTHER PUBLICATIONS

International Search Report, International Application No. PCT/US2016029305, dated Aug. 8, 2016, 2 Pages.
(Continued)

*Primary Examiner* — Kaitlyn E Smith
*Assistant Examiner* — Yasamin Ekrami
(74) *Attorney, Agent, or Firm* — Polansky & Associates, P.L.L.C.; Paul J. Polansky

(57) ABSTRACT

In one form, a projection frame eyelid heater includes a heating element, a frame, and a plurality of flexible standoffs. The heating element has first and second heat producing areas separated by a distance corresponding to a separation of human eyes and having first and second ends. The heating element produces heat in response to an application of a voltage thereto. The frame includes a left temple attachment portion and a right temple attachment portion each having a respective back portion extending downward and inward. The plurality of flexible standoffs is for attaching the heating element to the frame. In another form, the projection frame eyelid heater is combined with first and second insulated wires having first ends connected to the heating element, and second ends, to form an eye mask system.

42 Claims, 10 Drawing Sheets

Related U.S. Application Data which is a continuation-in-part of application No. 13/936,301, filed on Jul. 8, 2013, now abandoned.

(60) Provisional application No. 62/155,308, filed on Apr. 30, 2015.

(52) U.S. Cl.
CPC .............. *A61F 2007/0004* (2013.01); *A61F 2007/0071* (2013.01); *A61F 2007/0077* (2013.01); *A61F 2007/0078* (2013.01); *A61F 2007/0223* (2013.01); *A61F 2007/0228* (2013.01)

(58) Field of Classification Search
CPC ...... A61F 2007/0228; A61F 2007/0004; A61F 2007/0078; A61F 2007/0071
See application file for complete search history.

(56) References Cited

U.S. PATENT DOCUMENTS

| | | | | |
|---|---|---|---|---|
| 3,544,204 | A * | 12/1970 | Bienenfeld | G02C 5/20 2/448 |
| 4,261,364 | A | 4/1981 | Haddad et al. | |
| 5,126,533 | A * | 6/1992 | Newman | H01L 39/2422 219/200 |
| 6,155,995 | A | 12/2000 | Lin | |
| 6,263,158 | B1 * | 7/2001 | Rutherford | H05B 3/36 219/544 |
| 6,283,931 | B1 * | 9/2001 | Augustine | A61F 7/007 602/14 |
| 7,976,573 | B2 | 7/2011 | Korb et al. | |
| 2004/0187198 | A1 * | 9/2004 | Chiang | A63B 33/002 2/445 |
| 2007/0060988 | A1 * | 3/2007 | Grenon | A61F 9/00 607/96 |
| 2008/0132978 | A1 | 6/2008 | Korb et al. | |
| 2012/0222192 | A1 | 9/2012 | Carey et al. | |
| 2014/0025144 | A1 | 1/2014 | Ragan | |

FOREIGN PATENT DOCUMENTS

| | | |
|---|---|---|
| JP | H1085248 | 4/1998 |
| JP | 2006-198249 | 8/2006 |
| WO | WO 2003/061535 A1 | 7/2003 |
| WO | WO 2012/160496 A1 | 11/2012 |
| WO | WO 2014/133224 A1 | 9/2014 |
| WO | WO 2015/006115 A1 | 1/2015 |

OTHER PUBLICATIONS

Written Opinion of the International Searching Authority, International Application No. PCT/US2016029305, dated Aug. 8, 2016, 6 Pages.

P. Strøm-Tejsen, D.P. Wyon, L. Lagercrantz and L. Fang, "Occupant Evaluation of 7-Hour Exposures in a Simulated Aircraft Cabin—Part 1: Optimum Balance Between Fresh Air Supply and Humidity," Proceedings: Indoor Air 2005, pp. 40-45.

International Search Report and Written Opinion of International Application No. PCT/US2014/045187, dated Oct. 7, 2014, 14 pages.

Kevin Holzmeister, Recommendation Letter Regarding Blepharitis Treatment Mask, Aug. 23, 2013, 1 page.

\* cited by examiner

PROJECTION FRAME EYELID HEATER

This application is a continuation-in-part of application Ser. No. 14/311,573, filed Jun. 30, 2014, now U.S. Pat. No. 10,369,041, entitled "Eye Mask for Amelioration or Prevention of Dry Eye and the like," and invented by the inventor hereof, which is a continuation-in-part of application Ser. No. 13/936,301, filed Jul. 8, 2013, entitled "Eye Mask for Amelioration or Prevention of Dry Eye and the Like," and invented by the inventor hereof, now abandoned, and claims priority to provisional Application No. 62/155,308, filed Apr. 30, 2015, entitled "Projection Frame Eyelid Heater," invented by the inventor hereof, the contents of which are incorporated herein in their entirety.

FIELD

This disclosure relates generally to health devices, and more specifically to devices for the treatment of human eyes and/or eyelids.

BACKGROUND

In the human eye, the tear film covering the ocular surfaces is composed of three layers. The innermost layer in contact with the ocular surface is the mucus layer. The mucus layer is comprised of many mucins. The middle layer comprising the bulk of the tear film is the aqueous layer. The aqueous layer is important in that it provides a protective layer and lubrication to prevent dryness of the eye. Dryness of the eye can cause symptoms such as itchiness, burning, and irritation, which can result in discomfort. The outermost layer is comprised of many lipids known as "meibum" or "sebum." This outermost lipid layer is very thin, typically less than 250 nm in thickness. The lipid layer provides a protective coating over the aqueous and mucus layers to limit the rate at which these underlying layers evaporate. A higher rate of evaporation of the aqueous layer can cause dryness of the eye. Thus, if the lipid layer is not sufficient to limit the rate of evaporation of the aqueous layer, dryness of the eye may result. The lipid layer also lubricates the eyelid during blinking, which prevents dry eye. If the lipid layer can be improved, the rate of evaporation is decreased, lubrication is improved, and partial or complete relief of the dry eye state is achieved.

One environment which can contribute to dry eye is an airplane cabin. The interior of a pressurized airplane cabin has very low relative humidity, such as between 10 and 20%. Long airplane flights can severely irritate the eyes and cause dry eye.

Dry eye can also be caused by a condition known as meibomian gland dysfunction (MGD). Known treatments for MGD generally apply significant heat in order to melt, loosen, or soften of obstructions or occlusions in the meibomian glands. Regarding electrical heaters, one known eye treatment is described in U.S. Patent Pub. No. 2007/0060988. The heater it describes applies heat by using an electrical signal requiring the use of a thermocouple and sophisticated feedback control system to monitor and adjust the electrical signal to maintain heat between 43 and 47 degrees C. to one eye for between 1 and 10 minutes. Furthermore, the device uses a screw to adjust pressure on the eye. Because it requires 1) a threaded shaft or screw adjustment, 2) elevated heat, and 3) precise thermal regulation independent of temperature, the time of treatment, actual temperature, and pressure on the eye must be administered and monitored by a medical physician or technician to avoid burning the eyelid or damaging the eye itself. Another heater is described in U.S. Pat. No. 4,261,364. The heater it describes uses a battery operated surgical heater that warms a compress resembling an eye patch for post-ophthalmic surgery patients. The heater is strapped to a surgical compress that applies heat to a patient's eye socket. Since the heater 1) is in molded plastic not integrated with the compress, 2) is battery operated, 3) uses wiring for a heating element, and 4) heats a compress rather than an eyelid, the result is an uncomfortable, uncontrolled heat source that cannot carefully control the temperature that reaches the eyelid itself. Because of these factors, the time of treatment, actual temperature, and pressure on the eye must also be administered and monitored by a medical physician or technician to avoid burning the eyelid or damaging the eye itself.

Figure 1:
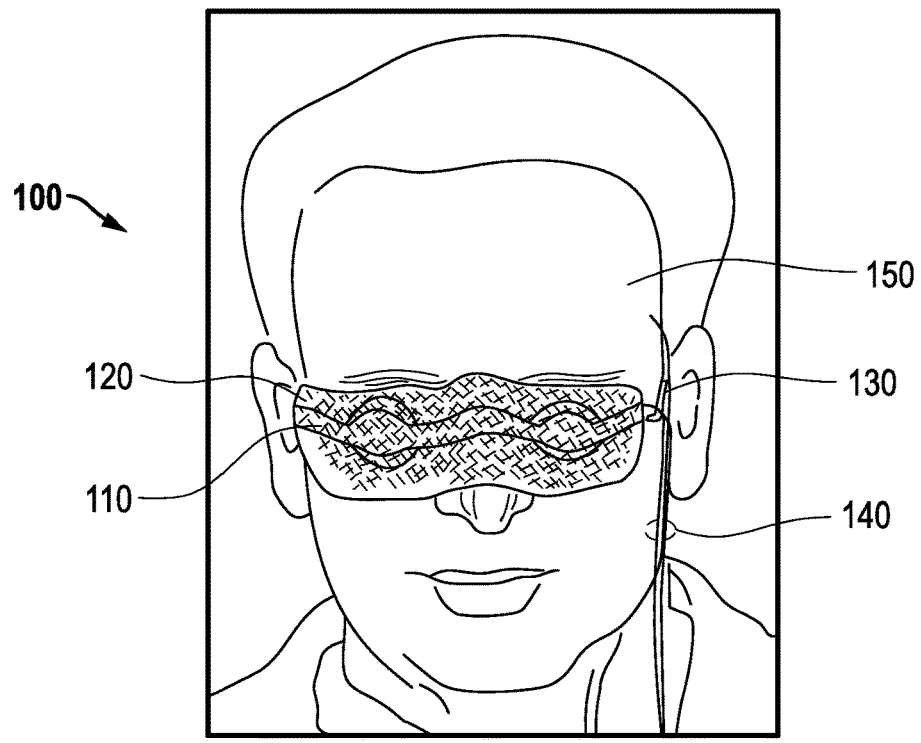
FIG. 1 illustrates a front view of an eye mask worn by a human according to some embodiments.

In the following description, the use of the same reference numerals in different drawings indicates similar or identical items. Moreover unless otherwise noted, the word "coupled" and its associated verb forms include both direct connection and indirect electrical connection by means known in the art, and unless otherwise noted any description of direct connection implies alternate embodiments using suitable forms of indirect electrical connection as well.

DETAILED DESCRIPTION OF ILLUSTRATIVE EMBODIMENTS

FIG. 1 illustrates a front view of an eye mask 100 worn by a human 150 according to some embodiments. Eye mask 100 includes an eye mask core assembly 110 surrounded by a covering 120 and attached just above the ears using a band 130 made of a suitable flexible material such as an elastomer (commonly referred to as an elastic). Eye mask 100 has a set of two insulated wires 140 attached to eye mask core assembly 110 on the left side (from the wearer's perspective) for connection to a suitable source of power as will be explained further below.

In general, eye mask 100 is intended to ameliorate dry eye and thus applies a lower amount of heating than known MGD eye treatment devices. In the illustrated embodiment, eye mask 100 increases the temperature of the surface of the eyelids by about 3-5 degrees Celsius (° C.) to about 40° C., and always keeps them at or below 43° C. This lower temperature allows the wearer to wear eye mask 100 for an extended and possibly indefinite period of time without eye damage or discomfort. Thus it is appropriate for use by an air traveler who may fall asleep and fail to remove it after 10 minutes. As will be explained below, eye mask 100 uses a resistive heating system that produces a relatively constant temperature and only requires the application of a relatively stable DC voltage, without the need for thermal feedback. Thus, eye mask 100 can be used with various power supplies and can be made cheaply.

Covering 120 effectively spreads and holds the heat generated by eye mask core assembly 110 across the whole surface of the eyelids, allowing low power dissipation. In one embodiment, covering 120 is formed by cotton cloth. When powered by a DC power supply of 5.0 volts, covering 120 is preferably formed with a cotton cloth about 0.25 mm thick. When powered by a DC power supply of 6.0 volts, covering 120 is preferably formed with a cotton cloth about 0.51 mm thick. Eye mask 100 is a hands-free mask that applies heat to both eyes and does not require a medical physician or technician for administration. Moreover it is adjustable for different wearers as will be described further below.

Figure 2:
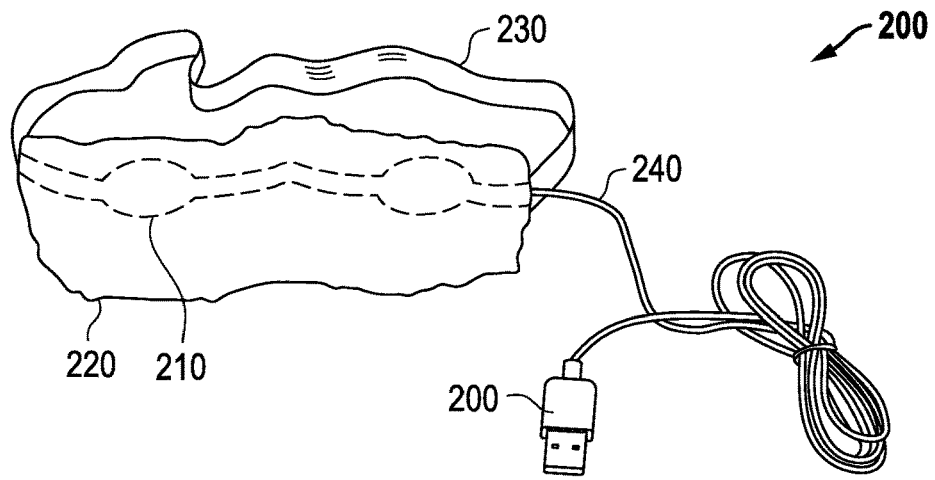
FIG. 2 illustrates a front view of an eye mask adapted for receiving power from a universal serial bus (USB) port according to one embodiment.

FIG. 2 illustrates a front view of an eye mask 200 adapted for receiving power from a universal serial bus (USB) port according to one embodiment. Eye mask 200 includes an eye mask core assembly 210 surrounded by a covering 220 and connected to a band 230 made of a suitable material such as elastic. Thus eye mask 200 can fit a variety of different head sizes, interpalprebal distances, and nasal bridge heights. Eye mask 200 has a cable 240 having two insulated wires. Cable 240 has a first end attached to eye mask core assembly 210 on the left side (from the wearer's perspective) and a second end electrically and mechanically attached to a USB connector 242. In this embodiment, eye mask 200 is capable of connecting to and receiving power from a USB host such as a laptop computer. Thus the user can power eye mask 200 using the laptop computer's battery. Typical laptop computer batteries are formed with lithium ion or lithium polymer technology which provides sufficient capacity to power the eye mask for an extended period of time. In addition some commercial airline flights provide a seat power jack which allows the laptop computer to be powered from the airplane's power supply, which avoids depleting the battery charge.

In another embodiment, connector 242 could be a connector substantially compliant with the American National Standards Institute/Society of Automotive Engineers ANSI/SAE J563 standard. This type of connector allows use by, for example, passengers in most automobiles and air travelers with seat power adaptors now available on many commercial airplanes.

Figure 3:
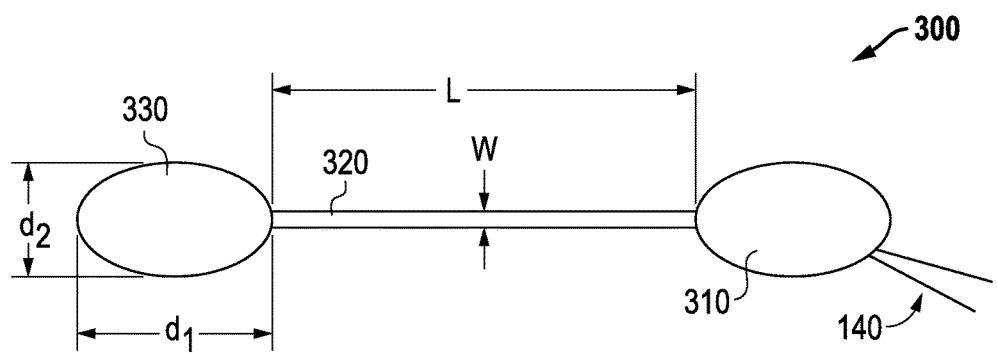
FIG. 3 illustrates a front view of a heating element suitable for use in the eye masks of FIGS. 1 and 2.

FIG. 3 illustrates a front view of a heating element 300 suitable for use in the eye masks of FIGS. 1 and 2. Heating element 300 includes two eye-shaped portions 310 and 330 separated by a center portion 320. Eye-shaped portion 310 is connected to wires 140 and has an internal conductor arranged in a pattern that is designed to produce heat, as will be explained further below. Eye-shaped portion 330 has a similar internal conductor pattern as eye-shaped portion 310. Center portion 320 has a conductor that is not designed to produce heat and electrically connects eye shaped portions 310 and 330.

In one embodiment, heating element 300 is sized for a typical adult. Each eye shaped portion has a longer diameter labeled "d1" of about 25.0-27.0 mm, and a shorter diameter labeled "d2" of about 14.0-17.0 mm. Center portion 320 has a length labeled "L" of about 66-67 mm, and a width labeled W of about 3-4 mm.

Figure 4:
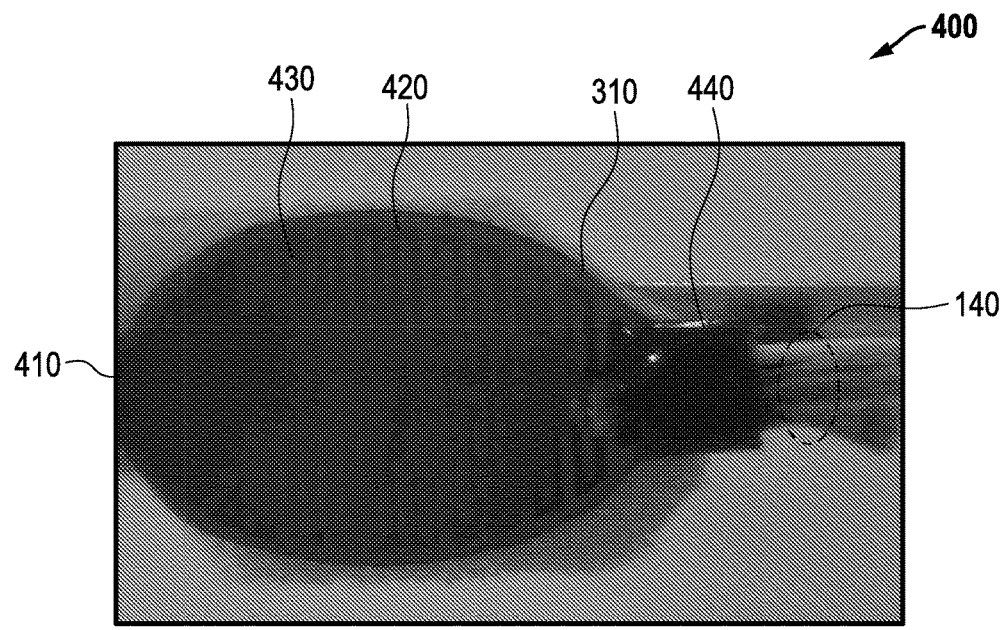
FIG. 4 illustrates a front view of a portion of the heating element of FIG. 3.

FIG. 4 illustrates a front view of a portion 400 of heating element 300 of FIG. 3. Portion 400 shows eye-shaped portion 310, which includes a first end 410 at the center portion, and a second end 440 for the physical and mechanical attachment of wires 140 to respective ends of a conductor 430. Conductor 430 is arranged in a serpentine pattern to increase the resistance and thus dissipate and distribute heat. The serpentine pattern is surrounded on a flexible substrate 420. Flexible substrate 420 is a thin polyimide film substrate having a thickness of about 0.33 millimeters (mm), which provides long flex life and ability to withstand metal etching processes. In one embodiment, conductor 430 is a trace formed with an alloy of nickel. It may be formed on flexible substrate 420 by any suitable process, such as depositing a blanket layer, applying a mask, and etching the serpentine pattern based on the mask.

Figure 5:
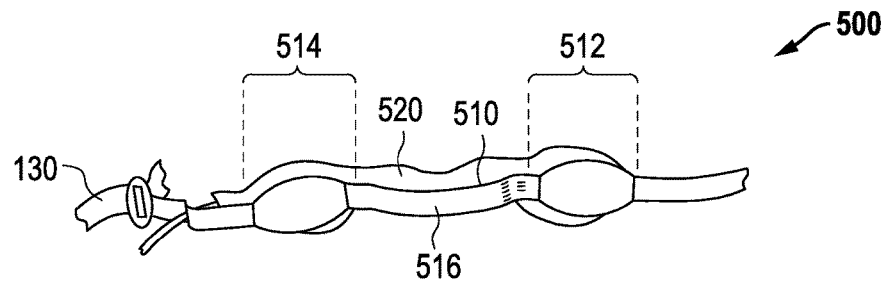
FIG. 5 illustrates a front view of a portion of the eye mask of FIG. 1 including an eye mask core assembly.

FIG. 5 illustrates a front view of a portion of the eye mask of FIG. 1 including an eye mask core assembly 500. Eye mask core assembly 500 includes a support member 510 attached to the first and second ends of band 130. Support member 510 in turn has two eye-shaped portions 512 and 514, respectively, separated by a rectangular center section 516 and surrounded by rectangular ends for attachment to band 130. Center section 516 has a bend in the center to form the eye mask around the bridge of the wearer's nose. Support member 510 is formed of any suitable semi-rigid material to hold the heating element substantially in place over the wearer's eyes. In some embodiments, the semi-rigid material is formed with aluminum having a thickness of about 0.010 mm to about 0.016 mm. Thus it can be adjusted by the user for different head sizes, interpalprebal distances, and nasal bridge heights. Eye mask core assembly 500 also includes a foam insulator 520 on the side of support member 510 closest to the wearer.

Figure 6:
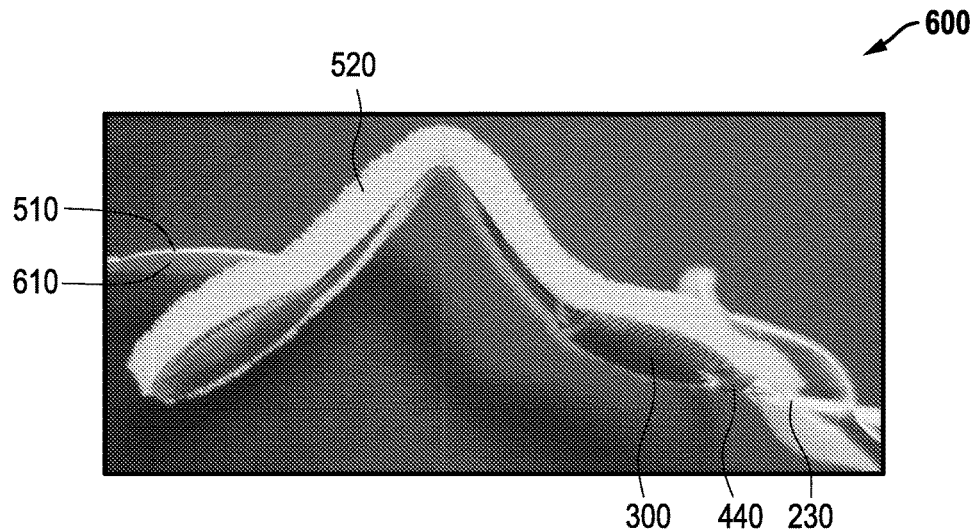
FIG. 6 illustrates a perspective view of an eye mask core assembly.

FIG. 6 illustrates a perspective view 600 of eye mask core assembly 500 of FIG. 5. As shown in FIG. 6, eye mask core assembly 600 includes support member 510 and heating element 300 separated by a foam insulator 520 that applies pressure to gently press heating element 300 against the wearer's eyes. Foam insulator 520 is attached to support member 510 by an adhesive 610 which may be any suitable hypoallergenic adhesive or glue that adheres to support member 510 and foam insulator 520. A similar hypoallergenic adhesive is used to attach heating element 300 to foam insulator 520.

Figure 7:
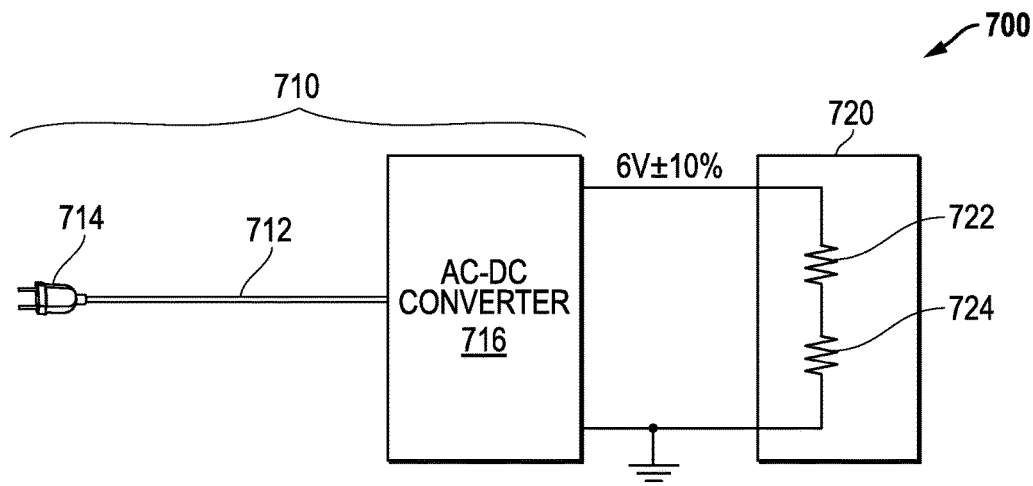
FIG. 7 illustrates in partial block diagram and partial schematic form an electrical diagram of an eye mask according to other embodiments.

FIG. 7 illustrates in partial block diagram and partial schematic form an electrical diagram of an eye mask system 700 according to another embodiment. Eye mask system 700 includes a regulated power supply 710 and a heating element 720 modeled as resistors 722 and 724 representative of the resistance of the serpentine conductor corresponding to the two eye-shaped portions. Eye mask system 700 uses regulated power supply 710 to connect to an alternating current (AC) mains supply and thus eye mask system 700 is suitable for home use. Regulated power supply 710 includes a wire 712 having a first end connected to an AC plug 714, and a second end connected to an AC-DC converter 716. AC-DC converter 716 is a low-cost converter formed with a transformer, an off-line switching regulator, and a small number of discrete components (not shown in FIG. 7) and provides an output voltage of 6 volts±10%.

Eye mask system 700 generates heat using resistive heating elements, and is a feed-forward system that does not require complicated thermal feedback to regulate the temperature at the surface of the wearer's eyelids to a precise temperature. Moreover the covering spreads the heat uniformly over the eyelids and provides temperature stability. Finally the low power dissipation makes it suitable for use with battery powered devices such as laptop computers for an extended period of time.

Figure 8:
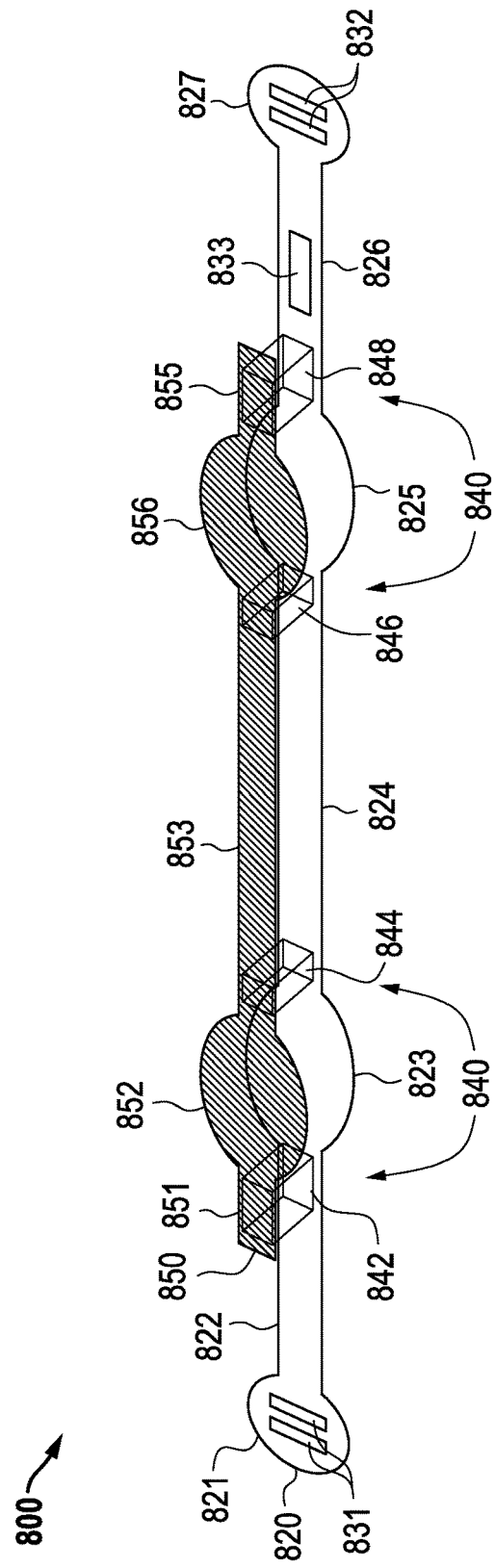
FIG. 8 illustrates a perspective view of an eye mask core assembly according to another embodiment.

FIG. 8 illustrates a perspective view of an eye mask core assembly 800 according to another embodiment. Eye mask core assembly 800 includes generally a support member 820, a set of standoffs 840, and a heating element 850. Support member 820 is underneath heating element 850 and includes generally a first band attachment portion 821, a first side portion 822, a first eye-shaped portion 823, a center nose portion 824, a second eye-shaped portion 825, a second side portion 826, and a second band attachment portion 827. First band attachment portion 821 has two vertical rectangular slits 831 etched or stamped therein, and second band attachment portion 827 likewise has two vertical rectangular slits 832 etched or stamped therein. A first end of the band is inserted in the inside one of vertical rectangular slits 831 and then looped back through the outer one of vertical rectangular slits 831. Likewise a second end of the band is inserted in the inside one of the vertical rectangular slits 832 and then looped back through the outer one of vertical rectangular slits 832. The elasticity of the bands allows the user to secure eye mask core assembly 800 comfortably to his or her head. An opening 833 is provided to connect and route the wires to heating element 850 away from the user's head.

Standoffs 840 include standoffs 842, 844, 846, and 848. Each standoff is made of a soft, flexible material such as foam and is attached to support member 820 at the sides of eye shaped portions 823 and 825 using a suitable adhesive. Likewise, the other ends of standoffs 840 are attached to corresponding portions of heating element 850. In the embodiment shown in FIG. 8, outer standoffs 842 and 848 are wider in width than inner standoffs 844 and 846.

Heating element 850 includes a first end 851, a first eye-shaped portion 852, a center portion 853, a second eye-shaped portion 854, and a second end 855. Eye-shaped portions 852 and 854 have substantially the same size and shape of eye-shaped portions 823 and 825 of support member 820. Second end 855 has exposed contacts for connection to a wire. Heating element 850 can be formed using a serpentine conductor as described above. In this additional embodiment, heating element 850 heats the surface of the eyelid to a temperature of about 40° C.

During construction of eye mask core assembly 800, the center portions 824 and 853 of support member 820 and heating element 850, respectively, are bent to correspond to the shape of a human nose. Moreover, each of ends 851 and 855 of heating element 850 are bent to fit conformally around the outer side of a corresponding one of standoffs 842 and 848. The end of the wire opposite the connector is inserted through opening 833 and glued to the inside of support member 820, and electrically and physically attached to the contacts of second end 855 of heating element 850 such as by soldering.

Eye mask core assembly 800 uses standoffs 840 to dispose the front sides of eye-shaped portions 852 and 854 adjacent to the surface of the eyes, while suspending their back sides in free space. Moreover standoffs 840 are formed of a soft, flexible material such as foam to gently dispose heating element 850 adjacent to the eyes. By avoiding placing any significant pressure on the eyelids, eye mask core assembly 800 allows the user to wear the eye mask for extended periods of time without being uncomfortable or damaging the user's corneas. Moreover eye mask core assembly 800 does not use a cover, reducing product cost while giving the eye mask the appearance of goggles used in tanning booths.

Eye mask core assemblies like eye mask core assembly 800 can be used with various chassis designs to form a wearable eye mask. In one embodiment described below, the wearable eye mask provides the benefits of low temperature eyelid heating as described above, and is also comfortable, wearable, manufacturable, and provides a universal fit to different users. For example, eye mask core assembly 800 can be used to form a projection frame eyelid heater. An embodiment of such a projection frame eyelid heater will now be described.

Figure 9:
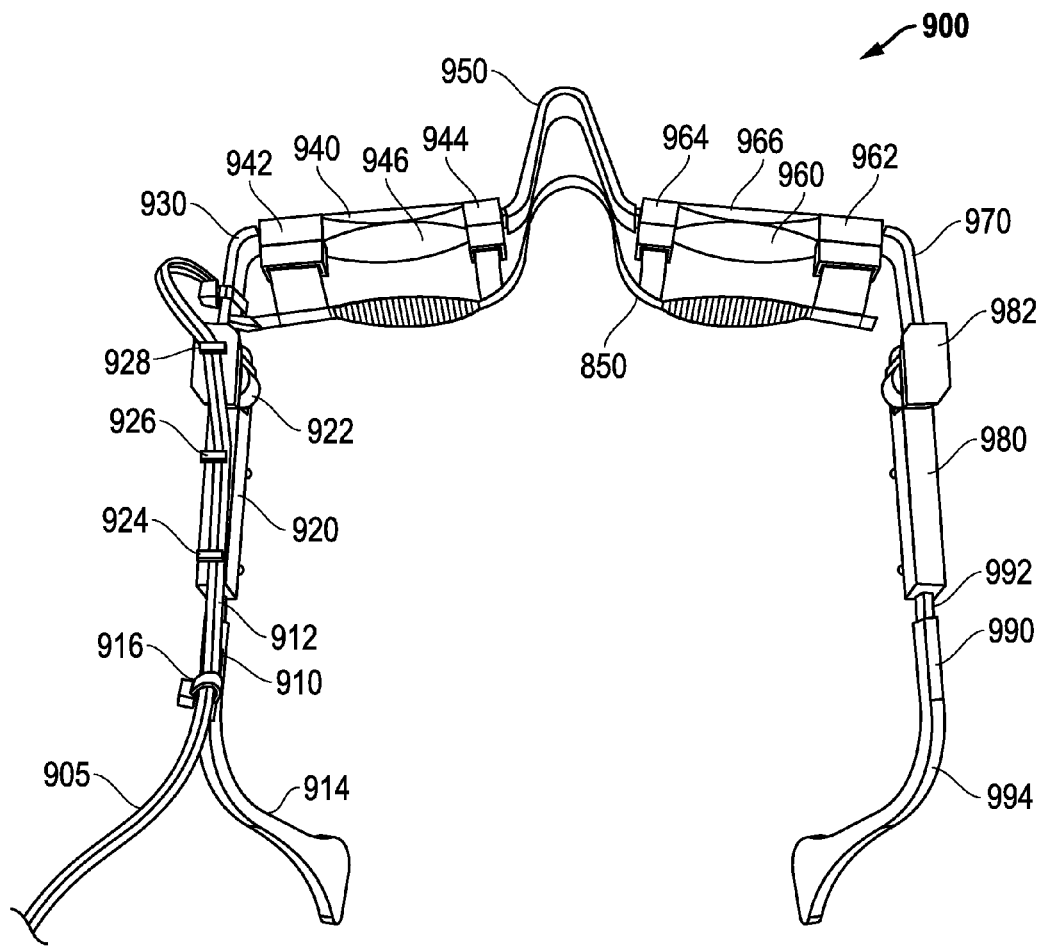
FIG. 9 illustrates a perspective view of a projection frame eyelid heater 900.

FIG. 9 illustrates a perspective view of a projection frame eyelid heater 900. Projection frame eyelid heater 900 includes generally heating element 850 constructed substantially as described above, and in addition includes generally a left temple portion 910, a left attachment member 920, a left corner member 930, a left eyelid chassis portion 940, an intermediate chassis portion 950, a right eyelid chassis portion 960, a right corner member 970, a right attachment member 980, and a right temple portion 990.

Left temple portion 910 includes a front portion 912, a back portion 914, and a loop 916. Front portion 912 is generally straight and has a slightly tapered front end with a small slightly protruding round pin, not visible in FIG. 9. Back portion 914 curves downward to fit over the left earlobe and inward to provide additional anchoring at the back of the user's head. Loop 916 allows wire 905 to move freely while still keeping wire 905 above the ear. This property allows the wire weight to increase the downward force above the ear, improving stability, and also allows left temple portion 910 to adjust within left attachment member 920 without binding the wire.

Left attachment member 920 fits over the tapered portion of front portion 912 at an adjustable location set when the pin of left temple portion 910 aligns with side holes of left attachment member 920 (not visible in FIG. 9). Left attachment member 920 includes a hinge portion 922 and wire guides 924, 926, and 928. Hinge portion 922 includes a vertical pin, not visible in FIG. 9. Left attachment member 920 uses wire guides 924, 926, and 928 to attach a wire 905 to left temple portion 910 and to secure wire 905 with suitable strain relief.

Left corner member 930 separates hinge portion 922 from the heating element 850 so that the left temple portion 910 and left attachment member 920 can fold inward for compact folding and storage. Left corner member 930 also forms a bend at approximately a right angle and includes a hole, not visible in FIG. 9, to allow wire 905 to connect to heating element 850.

Left eyelid chassis portion 940 attaches to left corner member 930 and includes an outer standoff receptacle 942, an inner standoff receptacle 944, and a beveled eye-shaped cover 946 located in the middle. A center portion of left eyelid chassis portion 940 also includes a set of holes, not visible in FIG. 9, for adjustment with intermediate chassis portion 950.

Intermediate chassis portion 950 is generally nose shaped but as will be described below, only fits around the nose without a requirement of being in contact with it. Intermediate chassis portion 950 includes a left and right portion each with a small slightly protruding round pin. The small round pin of the left portion mates with a corresponding hole on left eyelid chassis portion 940 to allow projection frame eyelid heater 900 to be adjusted to fit the user's inter-pupil distance.

Right eyelid chassis portion 960 adjustably attaches to bridge member 950 as described above and includes an outer standoff receptacle 962, an inner standoff receptacle 964, and a beveled eye-shaped cover 966 located in the middle. A center portion of right eyelid chassis portion 960 also includes a set of holes, not visible in FIG. 9, such that the small round pin of the right side of intermediate chassis portion 950 mates with a corresponding hole on right eyelid chassis portion 960 to allow projection frame eyelid heater 900 to be adjusted to fit the user's inter-pupil distance.

Right corner member 970 provides a space to separate a right hinge from heating element 850 and to allow right attachment member 980 and right temple portion 990 to fold inward for storage. Right corner member 970 also forms a bend at approximately a right angle.

Right attachment member 980 includes a hinge portion 982 and wire guides underneath, generally not visible in FIG. 9. Hinge portion 982 includes a vertical pin, not visible in FIG. 9, for attachment to right corner member 970 which allows it to pivot to allow right attachment member 980 and right temple portion 990 to fold inward for storage. Right attachment member 980 has the same structure as left attachment member 980 but is rotated such that wire guides corresponding to wire guides 924, 926, and 928 of left attachment member 920 are on the bottom side. Right attachment member 980 has a set of side holes, not visible in FIG. 9, to allow the tapered portion of right temple portion 990 to slide in to an adjustable location set when the pin of right temple portion 990 aligns with an a desired side hole of right attachment member 980.

Right temple portion 990 includes a front portion 992 and a back portion 994. Front portion 992 is generally straight and has a slightly tapered front end with a small slightly protruding round pin, not visible in FIG. 9. Back portion 994 curves downward to fit over the right earlobe and inward to provide additional anchoring at the back of the user's head. Note that right temple portion 990 and left temple portion 910 are not identical due to differences in orientation of the inward curve, and right temple portion 990 does not include a loop.

Heating element 850 is rotated one-hundred eighty degrees with respect to the orientation shown in FIG. 8, and is attached to foam standoffs 842, 844, 846, and 848 by any suitable method, such as by gluing. End 855 is attached to an end of wire 905.

Note that projection frame eyelid heater 900 is an eyelid heater, not a pair of glasses or swim goggles. The frame as shown in FIG. 9 is projected, eliminating the need for nose contact, support, or fitting. Because the frame is projected, the heating element conforms to the eyelid by adjusting the tension between the ear and the front of the projected frame, eliminating the need for any type of strap or band or any other object behind the head. The frame can be manufactured using any commercially available material, such as plastic, that is lightweight and has some flexibility.

Projection frame eyelid heater 900 has several features which allow the user to wear it comfortably for extended periods of time. First, projection frame eyelid heater 900 is not suspended on the nose using either intermediate chassis portion 950 or nose pads. Rather it is suspended in place due to the countervailing forces of the inward bends of temple portions 910 and 990, and the outward pressure of standoffs 842, 844, 846, and 848. In the illustrated embodiment, standoffs 842, 844, 846, and 848 are made of flexible foam. In other embodiments, they may be replaced by any suitable material that is compressive in a direction from heating element 850 the front of projection frame eyelid heater 900 that has memory and exerts a countervailing force when compressed. For example in one such embodiment, standoffs 842, 844, 846, and 848 could have an outer cover and a small inner spring such that it is compressive and exerts sufficient force to balance the inward bend of temple portions 910 and 990 but not so much force as to be uncomfortable to the user.

Second, projection frame eyelid heater 900 allows for a universal fit for various head shapes and inter-pupil (also known as inter-pupillary) distances. For example, standoffs 942, 944, 962, and 964 are placed around the periphery of the eye location, and the eye location is adjustable by changing the position of left eyelid chassis portion 940 and right eyelid chassis portion 960 with respect to intermediate chassis portion 960. These features account for epicanthal fold variations and craniofacial orbital protrusions of a wide variety of users, and projection frame eyelid heater 900 can used with almost any face and eye socket type. Moreover left and right temple attachment portions 910 and 990 are adjustable with respect to the front of projection frame eyelid heater 900 in a direction from the user's temples toward the user's left and right ears, respectively. These adjustments allow for almost any ear position and ear angulation. Hooking temple portions 910 and 990 that have been sized to fit the user's head around the user's ears provides the countervailing force to keep the front of the frame projected from the front of the user's face, with the eye portions of heating element 850 resting gently against the users eyelids with little corneal pressure. Also intermediate chassis portion 950 is nose shaped but has a size sufficient to fit around the user's nose for almost any nose size and shape, including a variety of nose nasofrontal angles, nasal root protrusions, nasal bridges, and nasal tips. Thus it is not necessary to provide a custom fit for each user by making various sub-sizes available, and the same projection frame eyelid heater can be adapted for almost any user.

Third, the design is easily manufactured using low-cost processes with only a small number of parts and a small number of assembly steps. The temple portions, attachment members, corner portions, front chassis portions, and bridge can be manufactured by a variety of processes including low-cost injection molding as well as three-dimensional (3D) printing.

Additional features, characteristics, and advantages of projection frame eyelid heater 900 will be apparent from observing it from various vantage points.

Figure 10:
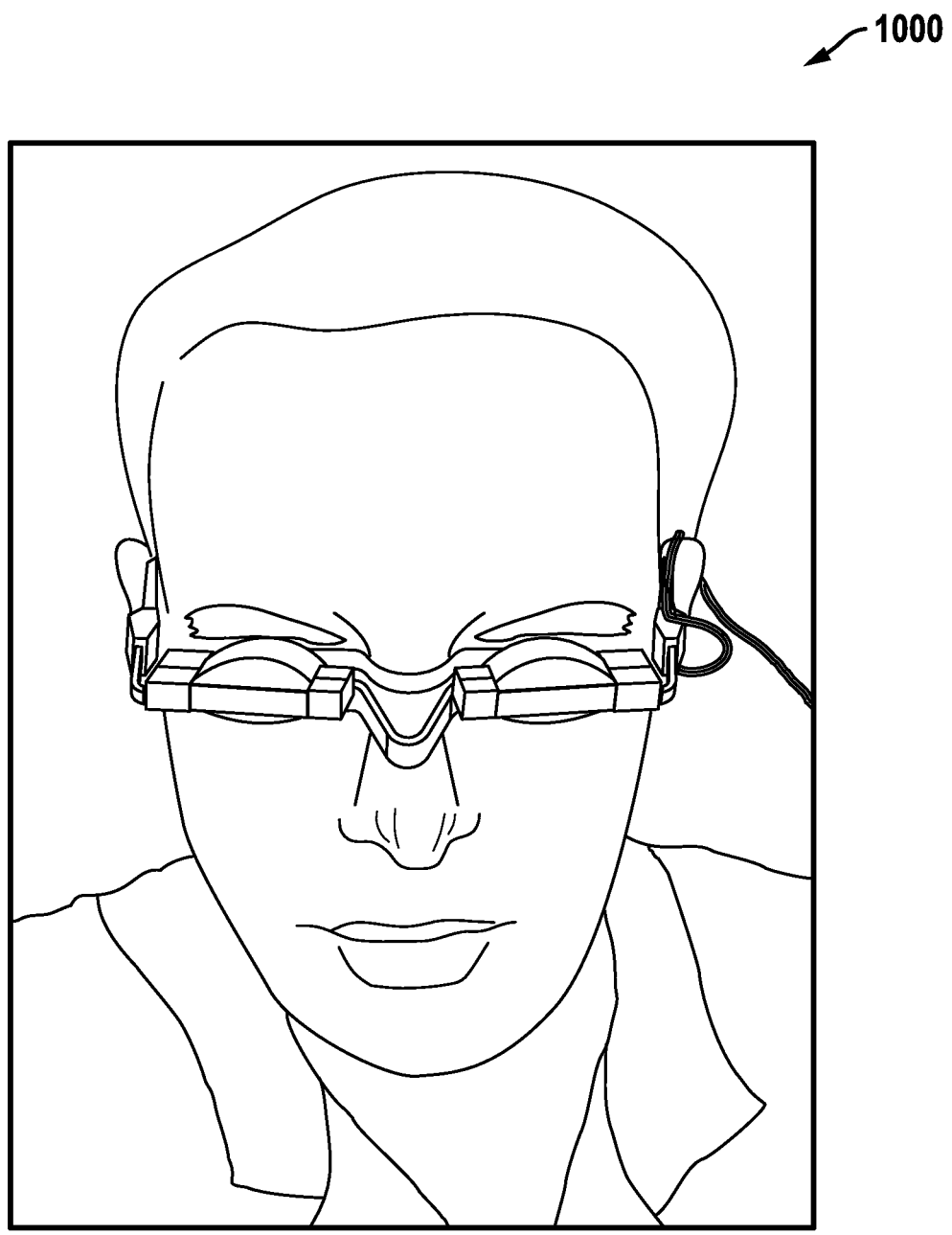
FIG. 10 is a front view of the projection frame eyelid heater of FIG. 9 worn by a human according to some embodiments.

FIG. 10 is a front view of projection frame eyelid heater 900 when worn by a human user.

Figure 11:
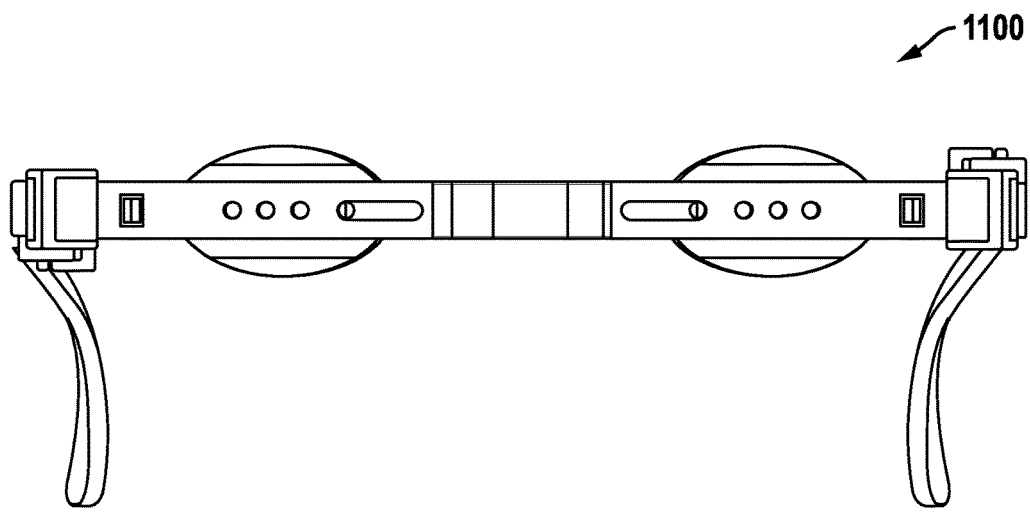
FIG. 11 is a front view of the projection frame of the projection frame eyelid heater FIG. 9.

FIG. 11 is a front view 1100 of the projection frame of projection frame eyelid heater 900 FIG. 9.

Figure 12:
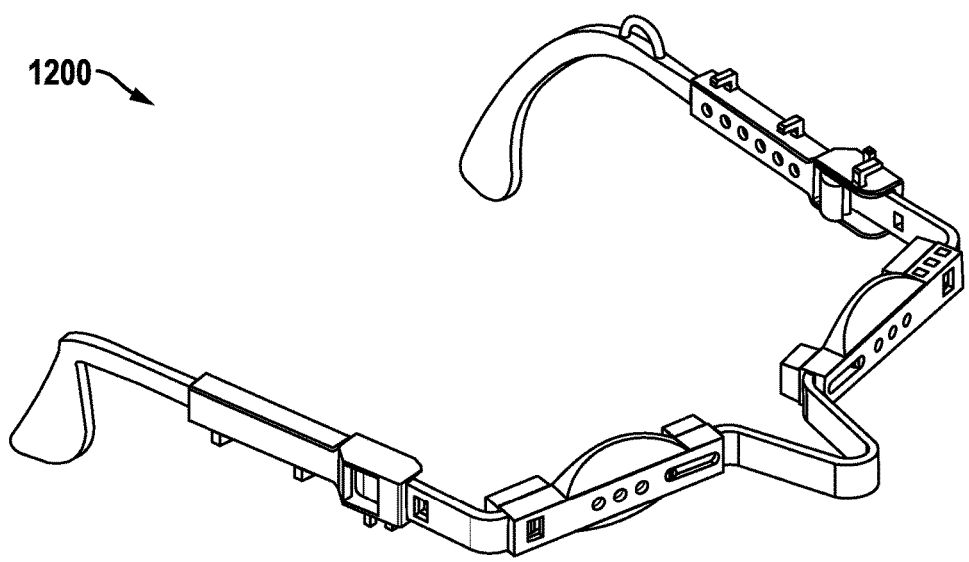
FIG. 12 is a top front right perspective view of the projection frame of the projection frame eyelid heater FIG. 9.

FIG. 12 is a top front right perspective view 1200 of the projection frame of projection frame eyelid heater 900 FIG. 9. View 1200 was generated using a computer-aided-design (CAD) program and is known as the International Standards Organization (ISO) "TFR" view.

Figure 13:
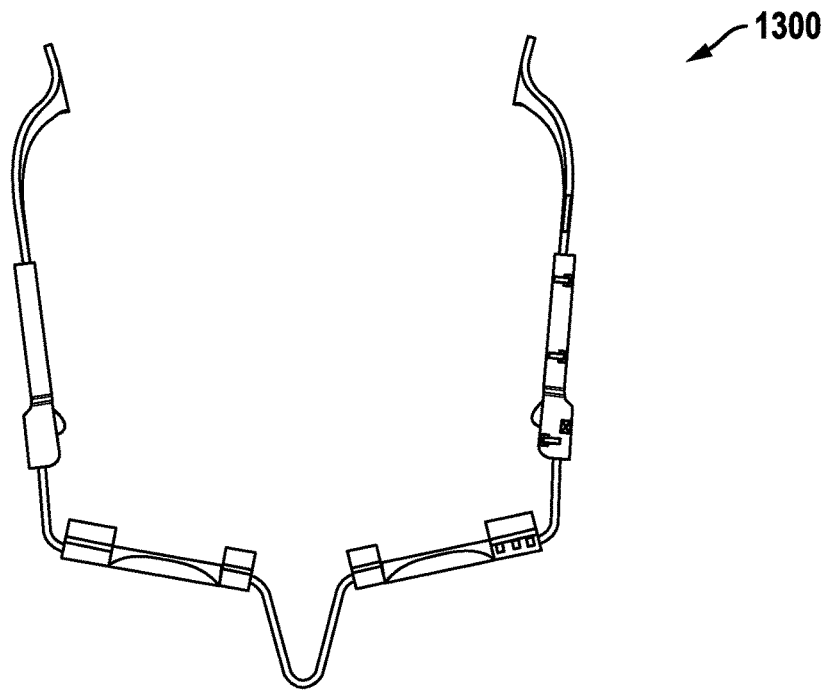
FIG. 13 is a top view of the projection frame of the projection frame eyelid heater FIG. 9.

FIG. 13 is a top view 1300 of the projection frame of projection frame eyelid heater 900 FIG. 9.

Figure 14:
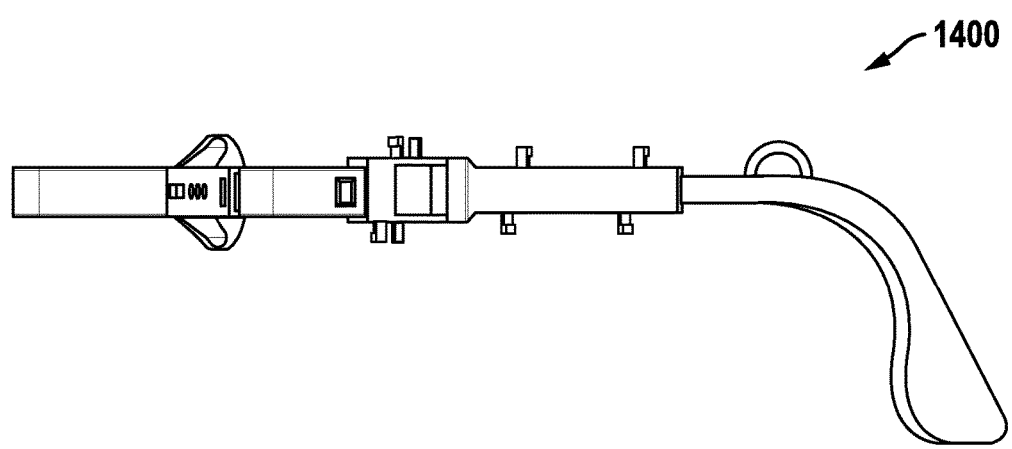
FIG. 14 is a left side view of the projection frame of the projection frame eyelid heater FIG. 9.

FIG. 14 is a left side view 1400 of the projection frame of projection frame eyelid heater 900 FIG. 9.

Figure 15:
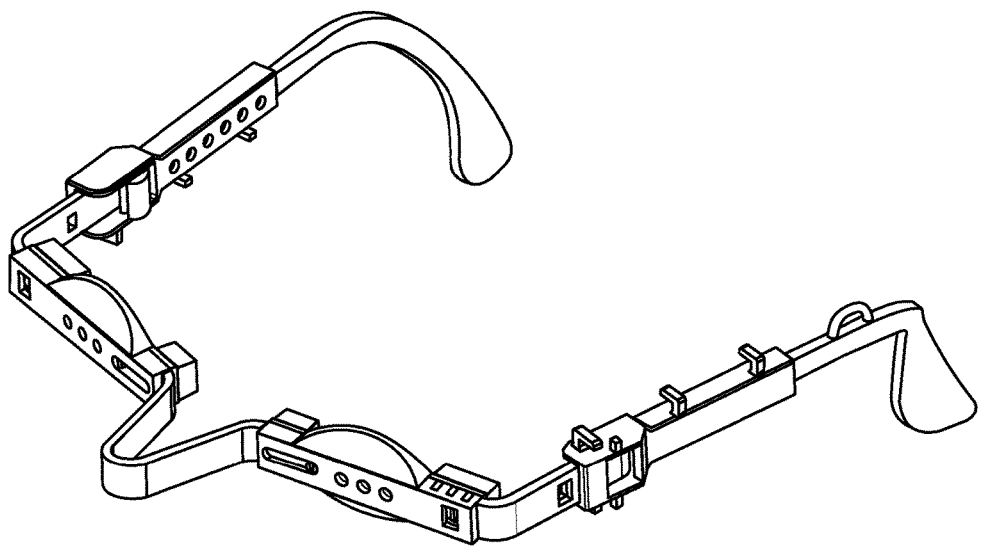
FIG. 15 is a top front left perspective view of the projection frame of the projection frame eyelid heater FIG. 9.

FIG. 15 is a top front left perspective view 1500 of the projection frame of projection frame eyelid heater 900 FIG. 9. View 1500 was generated using the CAD program and is known as the ISO "TFL" view.

Figure 16:
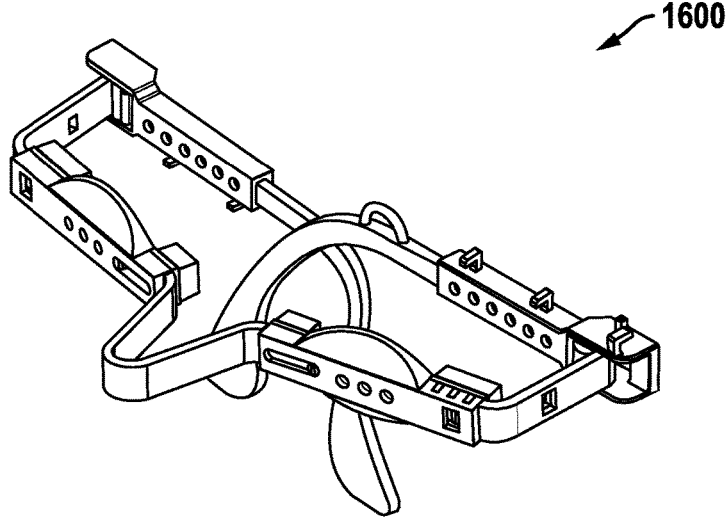
FIG. 16 is a top front left perspective view of the projection frame of the projection frame eyelid heater FIG. 9 when folded.

FIG. 16 is a top front left perspective view 1600 of the projection frame of projection frame eyelid heater 900 FIG. 9 when folded. View 1600 was also generated using the CAD program ISO TFL view.

Figure 17:
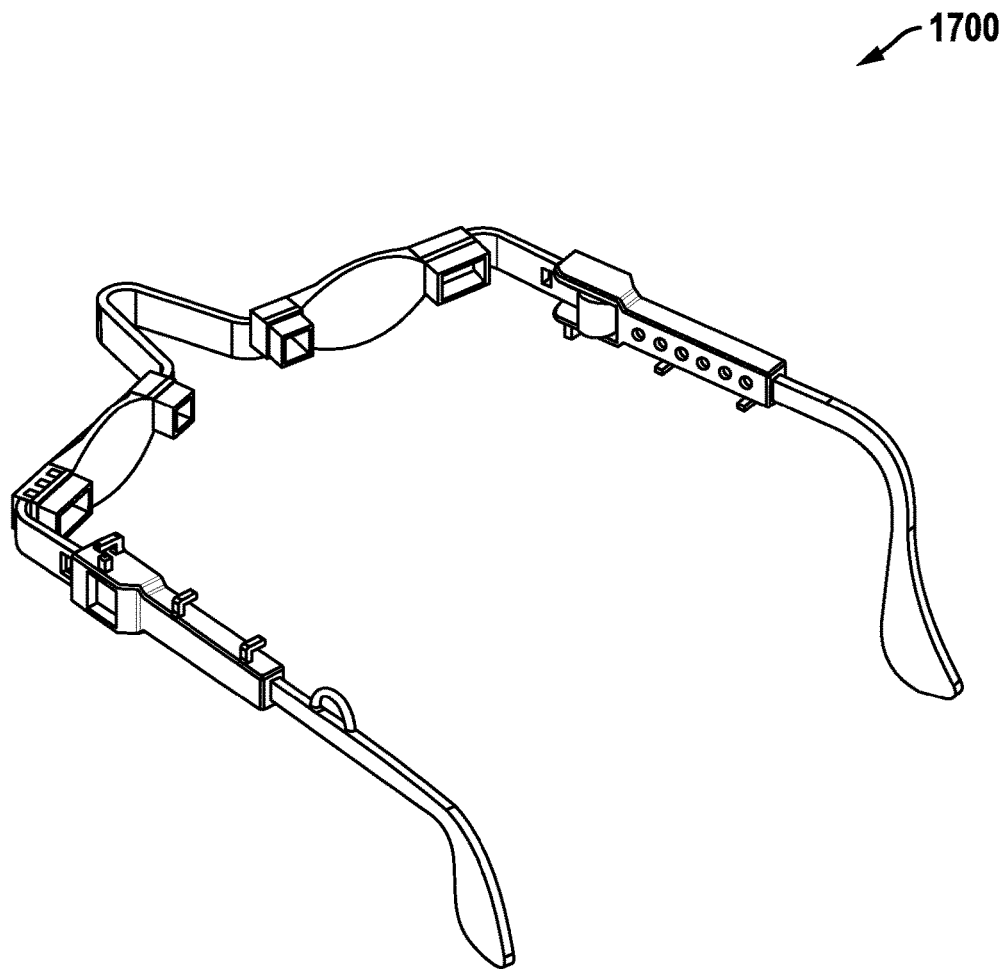
FIG. 17 is a top rear left perspective view of the projection frame of the projection frame eyelid heater FIG. 9.

FIG. 17 is a top rear left perspective view 1700 of the projection frame of projection frame eyelid heater 900 FIG. 9. View 1700 was generated using the CAD program and is known as the ISO "TRL" view.

Thus an eye mask has been described in various forms that ameliorates dry eye such as dry eye caused by meiobomian gland dysfunction, and dry eye that may be encountered in harsh environments such as low-humidity airplane cabins. In one form, the eye mask heats the eyelid to a lower temperature than known MGD treatments, such as 40° C., and thus is suitable for prolonged use. It operates using an eye mask core assembly surrounded by a covering such as a thin cotton cloth that spreads and holds the heat. The eye mask core assembly uses a heating element formed with a passive, serpentine conductor pattern formed on a flexible substrate. Since the heating element is formed with resistive elements, it can maintain an appropriate temperature without expensive thermal feedback and only requires the application of a relatively constant DC voltage obtainable from readily available power sources or generated from an AC mains power source using inexpensive components.

While various materials have been described for different components of the eye mask, it should be apparent that other suitable materials exist and may be used in place of those described above. For example, it is believed that covering 120 could be formed with a nylon covering of a suitable thickness instead of cotton. In the disclosed embodiments, the eye mask is held over the wearer's eyes using an elastic band surrounding the wearer's head. In other embodiments, the band can take other forms such as metal or plastic arms that fit over the wearer's ears like eyeglass arms. Moreover while different types of power supplies have been described, many other readily available power supplies may be used as well and at various voltages such as 5.5 volts, as long as the voltages and covering materials keep the eye temperature at a slightly elevated range.

Moreover these principles can be used to form a projection frame eyelid heater that is comfortable to the user, provides a universal fit, and is easily manufactured.

Accordingly, it is intended by the appended claims to cover all modifications of the invention that fall within the true scope of the invention.

What is claimed is:

1. A projection frame eyelid heater, comprising:
a heating element having first and second heat producing areas separated by a distance corresponding to a separation of human eyes and having first and second ends, said heating element producing heat in response to an application of a voltage thereto;
a frame including a left temple attachment portion and a right temple attachment portion each having a respective back portion extending downward and inward; and
a plurality of flexible standoffs for attaching the heating element to the frame, wherein said plurality of flexible standoffs comprises:
first and second standoffs each having a first end attached to said heating element and a second end attached to said frame such that said first end of said first standoff is attached to said heating element to the left of said first heat producing area and said first end of said second standoff is attached to said heating element to the right of said first heat producing area; and
third and fourth standoffs each having a first end attached to said heating element and a second end attached to said frame such that said first end of said third standoff is attached to said heating element to the left of said second heat producing area and said fourth standoff is attached to said heating element to the right of said second heat producing area.

2. The projection frame eyelid heater of claim 1, wherein said heating element comprises a flexible material.

3. The projection frame eyelid heater of claim 2, wherein said flexible material has a thickness of about 0.33 mm.

4. The projection frame eyelid heater of claim 3, wherein said flexible material comprises a polyimide film.

5. The projection frame eyelid heater of claim 1, wherein of said heating element comprises a conductor having a serpentine pattern in said first and second heat producing areas and a low-heat pattern in a center portion.

6. The projection frame eyelid heater of claim 5, wherein said conductor is formed with an alloy film.

7. The projection frame eyelid heater of claim 6, wherein said conductor is formed with a nickel alloy film.

8. The projection frame eyelid heater of claim 1, wherein said heating element provides heat upon application of a voltage of about 6.0 volts.

9. The projection frame eyelid heater of claim 1, further comprising:
first and second insulated wires having first ends connected to said heating element, and second ends for connection to a power supply.

10. The projection frame eyelid heater of claim 9, further comprising:
a connector coupled to said second ends of said first and second insulated wires and substantially compliant with the universal serial bus (USB) standard.

11. The projection frame eyelid heater of claim 9, further comprising:
a connector coupled to said second ends of said first and second insulated wires and substantially compliant with the ANSI/SAE J563 standard.

12. The projection frame eyelid heater of claim 9 further comprising:

a plug (714) for connection to an alternating current (AC) mains outlet and coupled to said second ends of said first and second insulated wires; and an AC-DC converter (716) having an input coupled to said first ends of said first and second insulated wires, and an output coupled to said heating element (720).

13. The projection frame eyelid heater of claim 1, wherein said frame comprises a plurality of receptacles for attachment to corresponding ones of said plurality of flexible standoffs.

14. The projection frame eyelid heater of claim 1, wherein each of said plurality of flexible standoffs is compressive in a direction from said heating element to a front of the projection frame eyelid heater.

15. The projection frame eyelid heater of claim 14, wherein when said plurality of flexible standoffs comprise foam.

16. The projection frame eyelid heater of claim 14, wherein when said plurality of flexible standoffs are formed using an outer cover and inner springs.

17. The projection frame eyelid heater of claim 1, further comprising:
a left eyelid chassis portion;
a right eyelid chassis portion; and
an intermediate chassis portion connecting said left eyelid chassis portion and said right eyelid chassis portion.

18. The projection frame eyelid heater of claim 17, wherein each of said left eyelid chassis portion and said right eyelid chassis portion is adjustable with respect to said intermediate chassis portion in a direction from the user's nose toward the user's left and right eyes, respectively.

19. The projection frame eyelid heater of claim 18, wherein each of said left temple attachment portion and said right temple attachment portion is adjustable with respect to said intermediate chassis portion in a direction from the user's temples toward the user's left and right ears, respectively.

20. The projection frame eyelid heater of claim 18, wherein each of said left temple attachment portion and said right temple attachment portion is adjustable with respect to said intermediate chassis portion in a direction from the user's temples toward the user's left and right ears, respectively.

21. The projection frame eyelid heater of claim 18, wherein said intermediate chassis portion is characterized as being nose shaped and has a size sufficient to fit around the user's nose.

22. An eye mask system, comprising:
a projection frame eyelid heater including left and right temple attachment portions and a front portion attached to a heating element having first and second eye-shaped portions through a plurality of flexible standoffs, said projection frame eyelid heater forming inward forces produced by said left and right temple attachment portions and countervailing outward forces produced by said flexible standoffs, wherein said plurality of flexible standoffs comprises:
first and second standoffs each having a first end attached to said heating element and a second end attached to said front portion such that said first end of said first standoff is attached to said heating element to the left of said first eye-shaped portion and said first end of said second standoff is attached to said heating element to the right of said first eye-shaped portion; and
third and fourth standoffs each having a first end attached to said heating element and a second end attached to said front portion such that said first end of said third standoff is attached to said heating element to the left of said second eye-shaped portion and said fourth standoff is attached to said heating element to the right of said second eye-shaped portion; and first and second insulated wires having first ends connected to said heating element, and second ends.

23. The eye mask system of claim 22, further comprising:
a power supply connected to said second ends of said first and second insulated wires for outputting a voltage thereto.

24. The eye mask system of claim 23, wherein said power supply comprises a battery.

25. The eye mask system of claim 22, wherein said heating element provides heat upon application of a voltage of about 6.0 volts.

26. The eye mask system of claim 22, further comprising:
first and second insulated wires having first ends connected to said heating element, and second ends for connection to a power supply.

27. The eye mask system of claim 22, further comprising:
a connector coupled to said second ends of said first and second insulated wires and substantially compliant with the universal serial bus (USB) standard.

28. The eye mask system of claim 22, further comprising:
a connector coupled to said second ends of said first and second insulated wires and substantially compliant with the ANSI/SAE J563 standard.

29. The eye mask system of claim 22 further comprising:
a plug (714) for connection to an alternating current (AC) mains outlet and coupled to said second ends of said first and second insulated wires; and
an AC-DC converter (716) having an input coupled to said first ends of said first and second insulated wires, and an output coupled to said heating element (720).

30. An eye mask system, comprising:
a projection frame eyelid heater comprising:
a heating element having first and second heat producing areas separated by a distance corresponding to a separation of human eyes and having first and second ends, said heating element producing heat in response to an application of a voltage thereto;
a frame including a left temple attachment portion and a right temple attachment portion each having a respective back portion extending downward and inward; and
a plurality of flexible standoffs for attaching the heating element to the frame, wherein said plurality of flexible standoffs comprises:
first and second standoffs each having a first end attached to said heating element and a second end attached to said frame such that said first end of said first standoff is attached to said heating element to the left of said first heat producing area and said first end of said second standoff is attached to said heating element to the right of said first heat producing area; and
third and fourth standoffs each having a first end attached to said heating element and a second end attached to said frame such that said first end of said third standoff is attached to said heating element to the left of said second heat producing area and said fourth standoff is attached to said heating element to the right of said second heat producing area, and
first and second insulated wires having first ends connected to said heating element, and second ends.

31. The eye mask system of claim 30, further comprising:
a power supply connected to said second ends of said first and second insulated wires for outputting a voltage thereto.

32. The eye mask system of claim 30, wherein said heating element comprises a flexible material.

33. The eye mask system of claim 32, wherein said flexible material has a thickness of about 0.33 mm.

34. The eye mask system of claim 33, wherein said flexible material comprises a polyimide film.

35. The eye mask system of claim 30, wherein of said heating element comprises a conductor having a serpentine pattern in said first and second heat producing areas and a low-heat pattern in a center portion.

36. The eye mask system of claim 35, wherein said conductor is formed with an alloy film.

37. The eye mask system of claim 36, wherein said conductor is formed with a nickel alloy film.

38. The eye mask system of claim 30, wherein said frame comprises a plurality of receptacles for attachment to corresponding ones of said plurality of flexible standoffs.

39. The eye mask system of claim 30, wherein each of said plurality of flexible standoffs is compressive in a direction from said heating element to a front of the projection frame eyelid heater.

40. The eye mask system of claim 39, wherein when said plurality of flexible standoffs comprise foam.

41. The eye mask system of claim 39, wherein when said plurality of flexible standoffs are formed using an outer cover and inner springs.

42. The eye mask system of claim 30, further comprising:
a left eyelid chassis portion;
a right eyelid chassis portion; and
an intermediate chassis portion connecting said left eyelid chassis portion and said right eyelid chassis portion.

* * * * *